(12) United States Patent
Aida et al.

(10) Patent No.: US 8,026,277 B2
(45) Date of Patent: Sep. 27, 2011

(54) FLAVOR COMPOSITION OR FRAGRANCE COMPOSITION, PRODUCT CONTAINING THE FLAVOR COMPOSITION OR FRAGRANCE COMPOSITION, AND NOVEL ESTER COMPOUND

(75) Inventors: Takashi Aida, Kanagawa (JP); Tetsuya Nagasawa, Kanagawa (JP); Yuichiro Yamazaki, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 40 days.

(21) Appl. No.: 12/516,454

(22) PCT Filed: Nov. 2, 2007

(86) PCT No.: PCT/JP2007/071367
§ 371 (c)(1),
(2), (4) Date: Jun. 29, 2009

(87) PCT Pub. No.: WO2008/065851
PCT Pub. Date: Jun. 5, 2008

(65) Prior Publication Data
US 2010/0081725 A1 Apr. 1, 2010

(30) Foreign Application Priority Data
Nov. 27, 2006 (JP) .................. 2006-318366

(51) Int. Cl.
*A61K 31/21* (2006.01)
*C07C 51/16* (2006.01)
(52) U.S. Cl. ........................ 514/506; 562/524
(58) Field of Classification Search ........ 560/1
See application file for complete search history.

(56) References Cited

FOREIGN PATENT DOCUMENTS
JP 52-007427 * 7/1975
JP 57-156436 * 9/1982

OTHER PUBLICATIONS

Colonge, Jean et al., Primary-methyl-ethylenic alcohols, Bulletin de la Societe Chimique de France (1965), (3), 619-25. Both original document and translation.*

Nomura et al., Synthesis and Physiological Activity of Toluyl Esters from 5-methyl-2-phenyl-hexenal Derivatives, Nihon Yukagakkaishi (1999), 48(4), 339-346. Both original document and translation.*
Park et al., Facile Synthesis of -Ketoesters Mediated by Sml2: Reformatsky Reaction Type Selfcondensation, Tetrahedron Letters, 1995, 36(10): 1673-1674.*
Ono et al., Stereospecific Anti Radical Elimination Reaction from -Nitro Sulfones, J. Org. Chem., 1987, 52, 5111-5116.*
M. Nomura., et al., "Synthesis and Physiological Activity of Toluyl Esters from 5-Methyl-2-Phenyl-2-Hexenal Derivatives", Nihon Yukagakukaishi, 1999, 48(4), pp. 339-346.
N. Ono., et al., "A New Synthesis of Allylic Alcohols or their Derivatives via Reductive Elimination from γ-Phenylthio-β-Nitroalcohols with Tributyltinhydride" Tetrahedron Letters, 1984, 25 (46), pp. 5319-5322.
K. Tsukida., et al., "Application of a Shift Reagent in Nuclear Magnetic Resonance Spectroscopy. IV A Simple Method for Stereochemical Assignment and Simultaneous Determination of cis-trans Isomeric Trisbustituted Allyic Alcohols", Chemical & Pharmaceutical Bulletin , 1973, 21 (2), pp. 248-251.
G.M.C. Higgins, et al., "A Development in Olefin Syntehsis: The Reaction of Some Allylic Mesitoates with Aliphatic Grignard Reagents", Journal of the Chemical Society, Jan. 1965, pp. 702-712.
M. Indo., "Synthetic Aromachemicals", Chemistry and Product Knowledge, Kagaku Kogyo Nippo-Sha, Mar. 6, 1996, first impression of the first edition, p. 671. (in Japanese).
European Search Report issued in European Patent Application No. 07831101.6-1221, mailed Mar. 2, 2010.

* cited by examiner

*Primary Examiner* — Sreeni Padmanabhan
*Assistant Examiner* — Svetlana M. Ivanova
(74) *Attorney, Agent, or Firm* — McDermott Will & Emery LLP

(57) ABSTRACT

Disclosed is a 2-methyl-2-pentenyl ester represented by the general formula (1) [wherein R represents a hydrogen atom or a hydrocarbon group having 1 to 9 carbon atoms which may have a substituent]. The compound has a new-type, unprecedented aroma and/or flavor, particularly a fruity, greenish or floral aroma and/or flavor. The compound can be added to a flavor or fragrance composition in an amount of 0.001 to 30 wt %. The flavor or fragrance composition can be added to a cosmetic product, a toiletry product, a bath agent, a food, a beverage or a pharmaceutical product in an amount of 0.0001 to 30 wt %. All of the compounds of the general formula (1) are novel, except for those compounds of the general formula (1) wherein R represents a methyl group, an isopropyl group, a phenyl group or a mesityl group.

3 Claims, No Drawings

FLAVOR COMPOSITION OR FRAGRANCE COMPOSITION, PRODUCT CONTAINING THE FLAVOR COMPOSITION OR FRAGRANCE COMPOSITION, AND NOVEL ESTER COMPOUND

RELATED APPLICATIONS

This application is the U.S. National Phase under 35 U.S.C. §371 of International Application No. PCT/JP2007/071367, filed on Nov. 2, 2007, which in turn claims the benefit of Japanese Application No. 2006-318366, filed on Nov. 27, 2006, the disclosures of which Applications are incorporated by reference herein.

TECHNICAL FIELD

The present invention relates to a flavor composition or a fragrance composition, in particular, a flavor composition or a fragrance composition that contains carboxylic acid esters of 2-methyl-2-pentenol (2-methyl-2-pentenyl esters) that is a compound having excellent fruity, greenish or floral aroma and/or flavor. In addition, the present invention also relates to various kinds of products such as perfume or cosmetic products, toiletry products, bath agents, beverage or food products or medicines, which contain the flavor composition or fragrance composition above, and novel 2-methyl-2-pentenyl esters.

BACKGROUND ART

The fruity, greenish and floral aroma and/or flavor has been widely used as the flavor or fragrance for various kinds of beverage or food products, various kinds of perfume or cosmetic products, aromatics, and other sanitation materials. It is also widely known that among the fruity, greenish or floral flavor or fragrance, carboxylic acid esters of alcohols play a very important role as a top-note flavor that comes up firstly (see, for instance, Non-Patent Reference 1). However, the carboxylic acid esters of alcohols, which play an important role as a top-note odorant of the fruity, greenish or floral flavor or fragrance, are almost standardized. Accordingly, flavorists and perfumers who concoct the flavor or fragrance are always in demand for compounds having new-type aroma and/or flavor different from existing ones, from the viewpoint of featuring the top-note or differentiating from existing flavor compounds or fragrance compounds.

Non-Patent Reference 1: M. Indo, "Synthetic Aromachemicals, Chemistry and Product Knowledge (Enlarged and revised edition)", Kagaku Kogyo Nippo-Sha (Mar. 22, 2005), PP. 461 to 462

The present invention has been made in view of such situations as mentioned above and an object of the invention is to provide a compound having a new-type aroma and/or flavor different from existing ones, and also to provide a flavor composition or a fragrance composition having fruity, greenish or floral aroma and/or flavor, which contain this compound.

Further, another object of the present invention is to provide perfume or cosmetic products, toiletry products, bath agents, beverage or food products, and medicines having the fruity, greenish and floral aroma and/or flavor, which contain the aforementioned flavor composition or fragrance composition.

Under the circumstances described above, as a result of intensive studies and investigations, the present inventors have found that esters of 2-methyl-2-pentenol with a formic acid or a carboxylic acid having 1 to 9 carbon atoms, which may have a substituent, show unprecedented excellent fruity, greenish and floral aroma and/or flavor with high natural feeling and are very useful as a flavor material or a fragrance material.

Herein, 2-methyl-2-pentenol that is a synthesis raw material of the carboxylic acid ester of 2-methyl-2-pentenol is a well-known compound. The 2-methyl-2-pentenol is usually produced according to a known method such as a chemical reduction method in which 2-methyl-2-pentenal that is an aldol dimer of propion aldehyde is reduced with hydrogenated sodium borate or a catalytic hydrogen reduction method in which metal and an organometallic complex are used. Further, a carboxylic acid ester of 2-methyl-2-pentenol with new-type aroma and/or flavor, which is used in the flavor composition or fragrance composition of the invention, is obtained by esterification of 2-methyl-2-pentenol. As a method of the esterification of 2-methyl-2-pentenol, various known methods can be adopted.

Further, the carboxylic acid esters of 2-methyl-2-pentenol found this time and having new-type aroma and/or flavor are novel compounds except for an acetic ester, an isopropionic ester, a benzoic ester, a toluic ester and a mesitylic ester.

Accordingly, another object of the invention is as well to provide carboxylic acid esters of 2-methyl-2-pentenol, which have the new-type aroma and/or flavor.

Thus, the present invention came to completion by finding that an ester of a formic acid or a carboxylic acid, which have 2 to 10 carbon atoms and may have a substituent, with 2-methyl-2-pentenol have unprecedented excellent fruity, greenish or floral flavor and/or fragrance with high natural feeling and is very useful as a flavor material or a fragrance material, and also by providing, in addition to the above, new compounds.

DISCLOSURE OF THE INVENTION

The present invention relates to flavor compositions or fragrance compositions described in items [1] to [3], perfume or cosmetic products, toiletry products, bath agents, beverage or food products or medicines described in item [4] containing those flavor compositions or fragrance compositions, and novel 2-methyl-2-pentenyl esters described in item [5] below.

[1] A flavor composition or a fragrance composition containing at least one kind of 2-methyl-2-pentenyl esters represented by a formula (1):

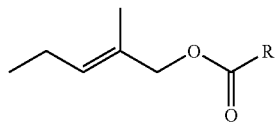

wherein, R represents a hydrogen atom or a hydrocarbon group having 1 to 9 carbon atoms, which may have a substituent.

[2] The flavor composition or the fragrance composition described in item [1] above, wherein the 2-methyl-2-pentenyl esters represented by the formula (1) above are 2-methyl-2-pentenyl acetate represented by a formula (2):

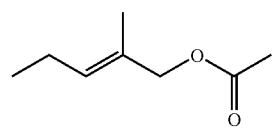

[3] The flavor composition or the fragrance composition described in item [1] or [2] above, wherein the 2-methyl-2-pentenyl esters compounded is added in an amount of 0.001 to 30% by weight in the flavor composition or fragrance composition.

[4] Perfume or cosmetic products, toiletry products, bath agents, beverage or food products or medicines, wherein the flavor composition or the fragrance composition described in any one of items [1] to [3] above is compounded in the range of 0.0001 to 3% by weight.

[5] 2-methyl-2-pentenyl esters represented by a formula (3):

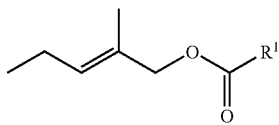

wherein, $R^1$ represents a hydrogen atom or a hydrocarbon group having 2 to 9 carbon atoms, which may have a substituent except for a methyl group, an isopropyl group, a phenyl group, a toluoyl group and a mesityl group.

ADVANTAGEOUS EFFECT OF THE INVENTION 2-methyl-2-pentenyl esters represented by the formula (1) of the invention, which include novel compounds, have strong, excellent fruity, greenish or floral aroma and/or flavor with natural feeling distinctly different from existing similar ones. The flavor compositions or fragrance compositions containing these are effectively used as flavor or fragrance of various kinds of beverage or food products, various kinds of perfume or cosmetic products, toiletry products, bath agents, and medicines including sanitation materials.

BEST MODE FOR CARRYING OUT THE INVENTION

Hereinafter, the present invention will be described in detail.

In the flavor composition or fragrance composition of the invention, 2-methyl-2-pentenyl esters represented by the formula (1) described above are used. Since the 2-methyl-2-pentenyl ester has a double bond in its molecule, two geometric isomers of the (E)-form and (Z)-form exist. The (E)-form and (Z)-form may be used alone or as a mixture thereof at an arbitrary ratio. The structure of 2-methyl-2-pentenol, which is a raw material, is almost (E)-form from the relation of the synthesis method of 2-methyl-2-pentenol. Therefore, 2-methyl-2-pentenyl ester of the (E)-form is preferably used from easiness of acquisition. In the formula, R is an acid residue of the ester and a hydrogen atom or a substituted or non-substituted hydrocarbon group having 1 to 9 carbon atoms. The hydrocarbon group having 1 to 9 carbon atoms may be any one of a substituted or non-substituted alkyl group, a substituted or non-substituted phenylalkyl group and a substituted or non-substituted aromatic group. Examples of the hydrocarbon group having 1 to 9 carbon atoms, which may have a substituent, include a methyl group, an ethyl group, a propyl group, an isopropyl group, a butyl group, a 2-methylpropyl group, a 1-methylpropyl group, a 1,1-dimethylethyl group, a pentyl group, a 3-methylbutyl group, a 2-methylbutyl group, a 1-methylbutyl group, a 1,2-dimethylpropyl group, a 1,1-dimethylpropyl group, a 2,2-dimethylpropyl group, a 1-ethylpropyl group, a 2-ethylpropyl group, a hexyl group, a 4-methylpentyl group, a 3-methylpentyl group, a 2-methylpentyl group, a 1-methylpentyl group, a 1,1-dimethylbutyl group, a 1,2-dimethylbutyl group, a 1,3-dimethylbutyl group, a 2,3-dimethylbutyl group, a 2,4-dimethylbutyl group, a 1-ethylbutyl group, a 2-ethylbutyl group, a heptyl group, a 5-methylhexyl group, a 4-methylhexyl group, a 3-methylhexyl group, a 2-methylhexyl group, a 1-methylhexyl group, a 1,1,2-trimethylbutyl group, a 1,1,3-trimethylbutyl group, a 2,2,3-trimethylbutyl group, a 2-methyl-2-ethylbutyl group, a 2-methyl-3-ethylbutyl group, an octyl group, a 6-methylheptyl group, a 5-methylheptyl group, a 4-methylheptyl group, a 3-methylheptyl group, a 2-methylheptyl group, a 1-methylheptyl group, a nonyl group, a 7-methyloctyl group, a 6-methyloctyl group, a 5-methyloctyl group, a 4-methyloctyl group, a 3-methyloctyl group, a 2-methyloctyl group, a 1-methyloctyl group, a phenylmethyl group, a phenyl group, a 1-methylphenyl group, a 2-methylphenyl group, a 3-methylphenyl group and a mesityl group, but not particularly limited thereto. Among these, substituted or non-substituted alkyl groups and a phenyl group are preferred, the alkyl groups that may have a substituent group are more preferred, and a methyl group is particularly preferred. Further, as the substituent group, alkyl groups are particularly preferred.

The 2-methyl-2-pentenyl esters represented by the formula (1) are produced by acylating 2-methyl-2-pentenol represented by a formula (4):

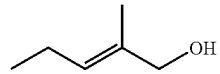

The acylation may be conducted according to any one of known methods. Examples thereof include a dehydrization and esterification method of 2-methyl-2-pentenol and carboxylic acid represented by RCOOH in the presence of an acid catalyst such as para-toluene sulfonic acid, and a reaction method of 2-methyl-2-pentenol and acid anhydride or acid halide of carboxylic acid represented by RCOOH. Reaction conditions of these acylations may be so far known conditions.

Further, 2-methyl-2-pentenol used in the acylation reaction may be one produced by any methods.

Examples of the carboxylic acid used when 2-methyl-2-pentenyl esters represented by the formula (1) are synthesized include saturated chain carboxylic acids and carboxylic acids containing an aromatic ring. Examples of the saturated chain carboxylic acid include formic acid, acetic acid, propionic acid, n-butyric acid, iso-butyric acid, valeric acid, iso-valeric acid, 2-methyl butyric acid, 2,2-dimethyl propionic acid, n-hexanoic acid, 4-methylvaleric acid, 3-methylvaleric acid, 2-methylvaleric acid, 2,3-dimethylbutyric acid, 3,3-dimethylbutyric acid, n-heptanoic acid, 5-methylhexanoic acid, 4-methylhexanoic acid, 3-methylhexanoic acid, 2-methylhexanoic acid, 4,4-dimethylvaleric acid, 3,4-dimethylvaleric acid, 2,4-dimethylvaleric acid, 3,3-dimethylvaleric acid, 2,3-dimethylvaleric acid, 4-ethylvaleric acid, 3-ethylvaleric acid, n-octanoic acid, 6-methylheptanoic acid, 5-methylheptanoic acid, 4-methylheptanoic acid, 3-methylheptanoic acid, 2-methylheptanoic acid, 5,5-dimethylhexanoic acid, 4,5-dimethylhexanoic acid, 3,5-dimethylhaxanoic acid, 2,5-dimethylhexanoic acid, 4,4-dimethylhexanoic acid, 3,4-dimethylhexanoic acid, 2,4-dimethylhexanoic acid, 3,3-dimethylhexanoic acid, 2,3-dimethylhexanoic acid, 3,4,4-trimethylvaleric acid, 2,4,4-trimethylvaleric acid, 3,3,4-trimethylvaleric acid, 2,3,4-trimethylvaleric acid, 2,2,4- trimethylvaleric acid, 2,3,3-trimethylvaleric acid, 2,2,3-trimethylvaleric acid, 3-ethyl-3-methylvaleric acid, 2-methyl-3-ethylvaleric acid, 2-ethyl-2-methylvaleric acid, 3-ethyl-4-methylvaleric acid, and 2-ethyl-4-methylvaleric acid, but not limited thereto.

Examples of carboxylic acid containing an aromatic ring include benzoic acid, o-toluic acid, m-toluic acid, p-toluic acid, 2,3-dimethylbenzoic acid, 2,4-dimethylbenzoic acid, 2,5-dimethylbenzoic acid, 2,6-dimethylbenzoic acid, 3,4-dimethylbenzoic acid, 3,5-dimethylbenzoic acid, 2,3,4-trimethylbenzoic acid, 2,3,5-trimethylbenzoic acid, 2,3,6-trimethylbenzoic acid, 2,4,5-trimethylbenzoic acid, 2,4,6-trimethylbenzoic acid, 3,4,5-trimethylbenzoic acid, phenylacetic acid, o-tolyl acetic acid, m-tolyl acetic acid, p-tolyl acetic acid, 2,3-dimethylphenylacetic acid, 2,4-dimethylphenylacetic acid, 2,5-dimethylphenylacetic acid, 2,6-dimethylphenylacetic acid, 3,4-dimethylphenylacetic acid, 3,5-dimethylphenylacetic acid, 1-phenylpropionic acid, 1-o-tolylpropionic acid, 1-m-tolylpropionic acid, 1-p-tolylpropionic acid, 2-phenylpropionic acid, 2-o-tolylpropionic acid, 2-m-tolylpropionic acid, and 2-p-tolylpropionic acid, but not limited thereto.

Further, these acids may be used, as required, as an form of acid anhydride or acid halide in the acylation reaction.

The 2-methyl-2-pentenyl esters represented by the formula (1) of the invention have unprecedented strong, excellent fruity, greenish and floral aroma and/or flavor with natural feeling, that is distinctly different from existing fruity, greenish or floral aroma and/or flavor. These esters, therefore, may be used as a flavor component and/or a fragrance component alone or in a combination of at least two kinds thereof. However, in general, ketones, aldehydes, esters, alcohols, ethers, terpenes, natural essential oils, and synthetic musks, which are well known as the flavor component and/or fragrance component, are compounded alone or in an appropriate combination with 2-methyl-2-pentenyl esters to prepare a flavor composition or a fragrance composition.

An amount of 2-methyl-2-pentenyl esters of the invention added into a flavor composition or a fragrance composition is set to an appropriate amount depending on flavor compositions or fragrance compositions to which the esters are added, or depending on the forms or usage forms of products to which the flavor composition or fragrance composition is further added. The amount of the esters compounded is usually preferably in the range of 0.001 to 30% by weight and particularly preferably in the range of 0.01 to 10% by weight relative to the flavor composition or fragrance composition.

The flavor composition or fragrance composition containing 2-methyl-2-pentenyl esters represented by the formula (1) may be preferably used as flavor or fragrance that is used in various products such as perfume or cosmetic products, toiletry products, bath agents, beverage or food products and medicines. The amount or application method of the flavor composition or fragrance composition obtained according to the invention to these products may appropriately be varied depending on the kind of the products and the purpose for use. The amount of the flavor composition or fragrance composition compounded to the product is usually 0.0001 to 30% by weight and preferably 0.001 to 10% by weight in the final product composition.

Perfume or cosmetic products, toiletry products, bath agents, beverage or food products or medicines, to which the flavor composition or the fragrance composition of the invention is applied, will be described below more in details.

Examples of perfume or cosmetic products to which the fragrance composition of the invention is applied include, for example, fragrance products, skin-care cosmetics, make-up cosmetics, hair cosmetics, anti-sunburn cosmetics, medicinal cosmetics, hair-care products, soaps, body lotions, bath agents, detergents, soft finishing agents, cleaning agents, kitchen detergents, breaching agents, aerosol agents, deodorant-aromatics, repellents, and other groceries.

More specifically, the examples include:

perfume, Eau de Parfum, Eau de Toilette, and Eau de Cologne as the fragrance products;

face washing cream, vanishing cream, cleansing cream, cold cream, massage cream, milky lotion, skin lotion, beauty wash, beauty pack, and make-up remover as skin-care cosmetics;

foundation, face powder, pressed powder, talcum powder, lipstick, lip cream, cheek rouge, eye liner, mascara, eye shadow, eyebrow-color, eye pack, nail enamel, and enamel remover as make-up cosmetics;

pomade, brilliantine, set lotion, hair stick, hair solid, hair oil, hair treatment, hair cream, hair tonic, hair liquid, hair spray, bandlin, hair-growing agent, and hair dye as hair cosmetics;

suntan products and sunscreen products as anti-sunburn cosmetics;

antiperspirant, after-shaving lotion and gel, permanent wave agent, medicinal soap, medicinal shampoo, and medicinal skin-care cosmetics as medicinal cosmetics;

shampoo, rinse, rinse-in-shampoo, hair conditioner, hair treatment, and hair pack as hair-care products;

toilet soap, bath soap, perfume soap, clear soap, and synthetic soap as soaps;

body soap, body shampoo, and hand soap as body cleaners;

heavy detergent for clothes, light detergent for clothes, liquid laundry detergent, laundry soap, compact detergent, and powder detergent as detergents;

softener and furniture care as soft finishing agents;

cleanser, house wash, toilet cleaner, bath cleaner, glass cleaner, fungicide, and cleaner for drain pipe as cleaning agents;

kitchen soap, kitchen synthetic soap, and dish wash as kitchen detergents;

oxidant bleach such as chlorine bleach and oxygen bleach, reductive bleach such as sulfur containing bleach, and optical bleach as bleaching agents;

spray type aerosol and powder spray as aerosol agents;

solid, gel and liquid deodorizer and aromatics as deodorant-aromatics; and tissue paper and toilet paper as groceries.

Examples of the toiletry products to which the flavor composition or fragrance composition of the invention is applied include toothpaste, tooth powder, oral wash, mouth wash, shaving cream, toilet lotion and the like.

Examples of the bath agent to which the fragrance composition of the invention is applied include bath agents such as bath salt, bath tablet and bath liquid, foam bath such as bubble bath, bath oil such as bath perfume and bath capsule, milk bath, bath jelly, and bath cube.

Examples of the beverage or food products to which the flavor composition of the invention include beverages such as fruit beverages, fruit spirits, milk-based drinks, carbonated drinks, soft drinks and health and nutrient drinks; frozen deserts such as ice creams, sherbets and popsicles; deserts such as jelly and puddings; confectionary such as cakes, cookies, chocolates and chewing gums; Japanese sweets such as bean-jam buns, thick jellied sweet made of azuki bean paste and thick jellied sweet made of powdered rice paste; jams; candies; breads; tea drinks and other favorite drinks such as green tea, oolong tea, black tea, persimmon leaf tea, chamomile tea, sasa veitchii tea, mulberry leaf tea, Houttuynia cordata tea, puaar tea, mate tea, rooibos tea, gymnema tea, guava tea, coffee and cocoa; soups such as Japanese style soups, Western style soups and Chinese style soups; flavored seasonings; various instant drinks and foods; and various snacks.

Examples of the medicines to which the flavor composition or fragrance composition of the invention is applied include, for example, skin external preparations such as poultice and ointment, internal preparations and the like.

However products to which the flavor composition or fragrance composition of the invention is applied are not limited to the products described above.

Further, appropriate components may be added to the products, to which the esters are applied, corresponding to usage purpose of each product and the products formed are provided as perfume or cosmetic products, toiletry goods, bath agents, beverage or food products or medicines. When the 2-methyl-2-pentenyl esters represented by the formula (1) described above are added to a product, the esters are preferably added in a state contained in the flavor composition or fragrance composition. However, the 2-methyl-2-pentenyl ester and a flavor or fragrance composition in which the esters are not contained may be added as separate compounding components.

EXAMPLES

Hereinafter, the present invention will be described specifically with reference to synthesis examples and examples. However, the invention is not at all limited thereto.

In synthesis examples and examples shown below, a nuclear magnetic resonance spectrum ($^1$H NMR), an infrared absorption spectrum (IR) and a mass spectrum (MS) were measured by use of following measurement devices.

Nuclear magnetic resonance spectrum ($^1$H NMR): DRX-500 (trade name) manufactured by Nippon Bruker Corporation.

Infrared absorption spectrum (IR): Nicolet AVATAR 360FT-IR (trade name) manufactured by Thermo Fischer Scientific Co., Ltd.

Mass spectrum (MS): GCMS-QP2010 (trade name) manufactured by Shimadzu Corporation.

Synthesis Example 1

Synthesis 1 of 2-Methyl-2-Pentenol

Into a 2 L reaction flask equipped with a thermometer and a reflux tube, 270.00 g of 2-methyl-2-pentenal (molecular weight: 98.15, 2.75 mol) and 600 ml of methanol were charged, followed by cooling it down to 0° C. with an ice-salt bath. Then 39.02 g of hydrogenated sodium borate (molecular weight: 37.83, 1.03 mol) was divided into 8 divisions and those was added into the solution one by one. As the reaction solution generated bubbles and heat by the addition of the hydrogenated sodium borate, it was cooled with an ice bath so as to maintain 5° C. or less. After the addition of hydrogenated sodium borate, the solution was stirred at 5° C. for 1 hour. Thereafter the ice bath was removed and the solution was stirred at room temperature for 1 hour. After the reaction solution obtained was quenched with 2 L diluted hydrochloric acid, the solution was extracted with 400 ml of toluene. The organic layer was separated and washed with an aqueous sodium hydrogen carbonate solution and brine. The organic solution obtained was dried with anhydrous magnesium sulfate and filtered. After the solvent in the organic solution was distilled away with a rotary evaporator under reduced pressure, the residue was distilled under reduced pressure, thus 259.60 g of the aimed 2-methyl-2-pentenol (molecular weight: 100.16, 2.59 mol) being obtained as a colorless transparent oily material. The yield was 94.2%. The by of the compound was 109 to 110° C./18890 Pa.

Measured values of the $^1$H NMR, IR and MS of the resultant compound were as shown below.

$^1$H NMR (500 MHz, CDCl$_3$, 8) ppm: 0.97 (t, J=7.6 Hz, 3H), 1.40 (s, 1H), 1.66 (s, 2H), 2.05 (qd, J=7.6 Hz, 7.6 Hz, 2H), 4.00 (s, 2H), 5.38-5.43 (m, 1H).

IR (NaCl) cm$^{-1}$: 3331, 2964, 2933, 2874, 1673, 1592, 1461, 1386, 1304, 1214, 1117, 1072, 1010, 854.

MS (m/e): 100, 85, 82, 71, 69, 67, 58, 57, 55, 53, 43, 41, 39.

Synthesis Example 2

Synthesis 2 of 2-Methyl-2-Pentenol

In a 100 ml autoclave made by stainless steel, 7.00 g of 2-methyl-2-pentenal (molecular weight: 98.15, 71.3 mmol), 328.7 mg of RuCl$_2$(PPh$_3$) (0.03 mmol), 2.4 ml of a 0.1 mole concentration isopropanol solution of 1,2-diaminoethane (0.24 mmol), and 15 ml of a 0.1 mol concentration isopropanol solution of potassium hydroxide (1.5 mmol) were charged under a nitrogen atmosphere, followed by stirring under a 10 atmospheric hydrogen pressure at room temperature for 3 hours. When the resulting reaction mixture was analyzed by a gas chromatography, a conversion rate was 100%. The reaction mixture was filtered, a filtrate was enriched with a rotary evaporator under reduced pressure, and the residue obtained was dissolved in toluene, followed by washing with saturated brine and then drying with anhydrous magnesium sulfate. Thereafter, the dried solution was enriched under reduced pressure and the oily material obtained was distilled under reduced pressure, thus 6.48 g of 2-methyl-2-pentenol (molecular weight: 100.16, 64.7 mmol) being obtained as a colorless transparent oily material. The yield was 90.8%.

Measured values of the $^1$H NMR, IR and MS thereof were same as those of Synthesis Example 1.

Synthesis Example 3

Synthesis of 2-Methyl-2-Pentenyl Acetate

Into a 200 ml reaction flask equipped with a thermometer, 20.00 g of 2-methyl-2-pentenol (molecular weight: 100.16, 199.7 mmol), 18.95 g of pyridine (molecular weight: 79.10, 239.6 mmol) and 100 ml of toluene were charged, and 22.4 g of acetic anhydride (molecular weight: 102.09, 219.7 mmol) was dropwise added thereto at room temperature over 40 minutes. When the reaction was monitored by a gas chromatography, 2-methyl-2-pentenol, that is a raw material, disappeared within 3 hours after addition of acetic anhydride. Thereafter 5 ml of methanol was added thereto, followed by stirring for 30 minutes. After 100 ml of diluted hydrochloric acid was added thereto to quench, 50 ml of toluene was added to extract and an organic layer was isolated. The isolated solution was sequentially washed twice with diluted hydrochloric acid and twice with saturated brine, followed by drying with anhydrous magnesium sulfate. The dried solution was filtered and the solvent therein was distilled away with a rotary evaporator under reduced pressure. The residue was distilled under reduced pressure, thus 26.6 g of aimed 2-methyl-2-pentenyl acetate (molecular weight: 142.20, 186.9 mmol) being obtained as a colorless transparent oily material. The yield was 93.6%. The by of the compound was 112 to 113° C./19420 Pa.

Measured values of the $^1$H NMR, IR and MS of the resultant compound were as shown below.

$^1$H NMR (500 MHz, CDCl$_3$, δ) ppm: 0.98 (t, J=7.5 Hz, 3H), 1.65 (s, 3H), 2.03-2.11 (m, 2H), 2.07 (s, 3H), 4.45 (s, 2H), 5.44-5.48 (m, 1H).

IR (NaCl) cm$^{-1}$: 2966, 2936, 2876, 1744, 1460, 1376, 1233, 1053, 1024, 980, 910, 850.

MS (m/e): 142, 127, 113, 100, 82, 71, 67, 55, 43, 41, 39.

Synthesis Example 4

Synthesis of 2-Methyl-2-Pentenyl Propionate

Into a 200 ml reaction flask equipped with a thermometer, a Dean-Stark tube and a reflux tube, 20.0 g of 2-methyl-2-pentenol (molecular weight: 100.16, 199.7 mmol), 20.7 g of propionic acid (molecular weight: 74.08, 279.6 mmol), 300 mg of p-toluene sulfonic acid monohydrate (molecular weight: 190.22, 1.6 mmol) and 100 ml of toluene were charged, followed by refluxing under heating while generated water was removed via a Dean-Stark tube. At 3 hours after the start of the reflux, water generation became unobservable. When the reaction was monitored at this point by a gas chromatography, 2-methyl-2-pentenol, that is a raw material, was confirmed disappeared. The heating was stopped and the reaction solution was cooled down to room temperature. After an aqueous solution of sodium carbonate was added thereto, the mixture was stirred for 10 minutes. Thereafter an organic layer was separated, followed by washing with saturated brine and then drying with anhydrous magnesium sulfate. After filtration thereof, the solvent in the organic solution was distilled away with a rotary evaporator under reduced pressure, and the residue was distilled under reduced pressure, thus 28.0 g of aimed 2-methyl-2-pentenyl propionate (molecular weight: 156.23, 179.3 mmol) being obtained as a colorless transparent oily material. The yield was 89.8%. The by of the compound was 97-99° C./5187 Pa.

Measured values of the $^1$H NMR, IR and MS of the resultant compound were as shown below.

$^1$H NMR (500 MHz, CDCl$_3$, δ) ppm: 0.97 (t, J=7.6 Hz, 3H), 1.15 (t, J=7.6 Hz, 3H), 1.65 (s, 3H), 2.04 (qd, J=7.6 Hz, 7.6 Hz, 2H), 2.35 (q, J=7.6 Hz, 2H), 4.46 (s, 2H), 5.43-5.49 (m, 1H).

IR (NaCl) cm$^{-1}$: 2966, 2938, 2877, 1740, 1463, 1377, 1343, 1274, 1182, 1082, 1012, 949, 896, 852.

MS (m/e): 156, 141, 127, 113, 100, 83, 82, 67, 57, 55, 41, 39.

Synthesis Example 5

Synthesis of 2-Methyl-2-Pentenyl Butyrate

Into a 200 ml reaction flask equipped with a thermometer, 20.00 g of 2-methyl-2-pentenol (molecular weight: 100.16, 199.7 mmol), 18.95 g of pyridine (molecular weight: 79.10, 239.6 mmol) and 100 ml of toluene were charged, and then 34.8 g of butyric anhydride (molecular weight: 158.20, 219.7 mmol) was dropwise added thereto at room temperature over 40 minutes. When the reaction was monitored by a gas chromatography, 2-methyl-2-pentenol, that is a raw material, disappeared at 4 hours after the addition of the butyric anhydride. To the solution, 5 ml of methanol was added, followed by stirring for 30 minutes. Thereafter the solution was quenched by adding 100 ml of diluted hydrochloric acid and extract with 50 ml of toluene. The organic layer obtained was separated and then sequentially washed twice with diluted hydrochloric acid and twice with saturated brine, followed by drying with anhydrous magnesium sulfate. After the solvent in the organic solution was distilled away with a rotary evaporator under reduced pressure, the residue was distilled under reduced pressure, thus 31.4 g of the aimed 2-methyl-2-pentenyl butyrate (molecular weight: 170.25, 184.7 mmol) being obtained as a colorless transparent oily material. The yield was 92.5%. The by of the compound was 94 to 95° C./2260 Pa.

Measured values of the $^1$H NMR, IR and MS of the resulted compound were as shown below.

$^1$H NMR (500 MHz, CDCl$_3$, δ) ppm: 0.96 (t, J=7.5 Hz, 3H), 0.98 (t, J=7.6 Hz, 3H), 1.64 (s, 3H), 1.68 (tq, J=7.6 Hz, 7.5 Hz, 2H), 2.06 (dt, J=7.6 Hz, 7.2 Hz, 2H), 2.31 (t, J=7.5 Hz, 2H), 4.46 (s, 2H), 5.43-5.49 (m, 1H).

IR (NaCl) cm$^{-1}$: 2966, 2936, 2876, 1738, 1460, 1420, 1382, 1351, 1304, 1255, 1175, 1091, 1042, 979, 852.

MS (m/e): 170, 141, 127, 113, 100, 89, 82, 71, 67, 55, 43, 41, 39.

Synthesis Example 6

Synthesis of 2-Methyl-2-Pentenyl Benzoate

Into a 200 ml reaction flask equipped with a thermometer, 20.00 g of 2-methyl-2-pentenol (molecular weight: 100.16, 199.7 mmol), 18.95 g of pyridine (molecular weight: 79.10, 239.6 mmol) and 100 ml of toluene were charged, and then 30.9 g of benzoyl chloride (molecular weight: 140.57, 219.7 mmol) was dropwise added thereto at room temperature over 30 minutes. When the reaction was monitored by a gas chromatography, 2-methyl-2-pentenol, that is a raw material, disappeared at 1 hour after the addition of the benzoyl chloride. To the solution, 5 ml of methanol was added, followed by stirring for 30 minutes. Thereafter the solution was quenched by adding 100 ml of diluted hydrochloric acid and extracted with 50 ml of toluene. The organic layer was separate and then sequentially washed twice with diluted hydrochloric acid and twice with saturated brine, followed by drying with anhydrous magnesium sulfate. After filtration, the solvent in the organic solution was distilled away with a rotary evaporator under reduced pressure, the residue was distilled under reduced pressure, thus 37.2 g of the aimed 2-methyl-2-pentenyl benzoate (molecular weight: 204.27, 182.1 mmol) being obtained as a colorless transparent oily material. The yield was 91.2%. The by of the compound was 91 to 92° C./71 Pa.

Measured values of the $^1$H NMR, IR and MS of the resultant compound were as shown below.

$^1$H NMR (500 MHz, CDCl$_3$, δ) ppm: 1.00 (t, J=7.5 Hz, 3H), 1.73 (s, 3H), 2.09 (qd, J=7.5 Hz, 7.2 Hz, 2H), 4.71 (s, 2H), 5.56 (t, J=7.2 Hz, 1H), 7.44 (dd, J=7.8 Hz, 8.1 Hz, 2H), 7.55 (t, J=8.1 Hz, 1H), 8.06 (d, J=7.8 Hz, 2H).

IR (NaCl) cm$^{-1}$: 2965, 2934, 2874, 1720, 1061, 1585, 1452, 1390, 1370, 1314, 1273, 1176, 1111, 1070, 1026, 951, 851.

MS (m/e): 204, 189, 175, 161, 147, 131, 123, 105, 82, 77, 67, 55, 51, 43, 41, 39.

Example 1

Organoleptic Evaluation

The odors of 2-methyl-2-pentenyl acetate, 2-methyl-2-pentenyl propionate, 2-methyl-2-pentenyl butyrate, and 2-methyl-2-pentenyl benzoate, which were obtained in Synthesis Examples 3 to 6, were evaluated on a blotter by 7 expert panelists. Results are shown in Table 1.

TABLE 1

| Compound Name | Evaluation Result |
| --- | --- |
| 2-methyl-2-pentenyl acetate | Pear, melon and banana-like fruity odor |
| 2-methyl-2-pentenyl propionate | Herb-like fruity greenish odor |
| 2-methyl-2-pentenyl butyrate | Wood-like fruity greenish odor |
| 2-methyl-2-pentenyl benzoate | Fruity floral odor with violet note |

Example 2 and Comparative Example 1

Using 2-methyl-2-pentenyl acetate obtained in Synthesis Example 3, 100 g of a fruity greenish fragrance composition was prepared according to the prescription shown below as Example 2 and 100 g of a fragrance composition that does not contain 2-methyl-2-pentenyl acetate was prepared as Comparative Example 1. The aromas of these fragrance compositions were evaluated by 7 expert panelists. Compounding amounts in the table are based on gram.

TABLE 2

| Component | Example 2 | Comparative Example 1 |
| --- | --- | --- |
| Ambretone | 50 | 50 |
| γ-Undecalactone | 25 | 25 |
| 2-Methyl-2-pentenyl acetate | 1 | — |
| 1% DPG solution of labdanum oil | 2.5 | 2.5 |
| Dipropylene glycol (DPG) | 21.5 | 22.5 |
| Total | 100 | 100 |

As a result of evaluation, all 7 panelists reported that the fragrance composition of Example 2 showed fruity greenish aroma higher in performance and natural feeling than the fragrance composition of Comparative Example 1.

Example 3 and Comparative Example 2

Banana Flavor

A flavor composition (banana flavor) was prepared with 2-methyl-2-pentenyl acetate obtained in Synthesis Example 3 according to a prescription shown below as Example 3 and a flavor composition (banana flavor) that does not contain 2-methyl-2-pentenyl acetate was prepared as Comparative Example 2. These flavor compositions were evaluated by 7 expert panelists. Compounding amounts in the table are based on parts by weight.

TABLE 3

| Component | Example 3 | Comparative Example 2 |
| --- | --- | --- |
| 2-Methyl-2-pentenyl acetate | 20.000 | — |
| Acetoin | 0.250 | 0.250 |
| Isoamyl acetate | 70.000 | 70.000 |
| Isoamyl butyrate | 30.000 | 30.000 |
| Isoamyl isovaleric acid | 15.000 | 15.000 |
| n-Butyl butyrate | 15.000 | 15.000 |
| Isobutyl butyrate | 15.000 | 15.000 |

TABLE 3-continued

| Component | Example 3 | Comparative Example 2 |
| --- | --- | --- |
| Ethyl acetate | 10.000 | 10.000 |
| Ethyl butyrate | 20.000 | 20.000 |
| Hexanal | 0.200 | 0.200 |
| Trans-2-hexanal | 0.400 | 0.400 |
| Cis-3-hexanal | 3.000 | 3.000 |
| δ-Dodecalactone | 0.100 | 0.100 |
| Butyric acid | 0.050 | 0.050 |
| Isovaleric acid | 0.050 | 0.050 |
| Propylene glycol (solvent) | 800.950 | 820.950 |
| Total | 1000.000 | 1000.000 |

As a result of evaluation, all 7 panelists reported that the flavor composition of Example 3 showed banana-like aroma higher in performance and natural feeling than the flavor composition of Comparative Example 2.

Example 4 and Comparative Example 3

Mango Flavor

A flavor composition (mango flavor) was prepared with 2-methyl-2-pentenyl acetate obtained in Synthesis Example 3 according to a prescription shown below as Example 4 and a flavor composition (mango flavor) that does not contain 2-methyl-2-pentenyl acetate was prepared as Comparative Example 3. These flavor compositions were evaluated by 7 expert panelists. Compounding amounts in the table are based on parts by weight.

TABLE 4

| Component | Example 4 | Comparative Example 3 |
| --- | --- | --- |
| 2-Methyl-2-pentenyl acetate | 20.000 | — |
| Dimethyl sulfide | 0.250 | 0.250 |
| Diisopropyl disulfide | 0.0500 | 0.0500 |
| Ethyl acetate | 30.000 | 30.000 |
| Ethyl butyrate | 5.000 | 5.000 |
| Ethyl hexanoate | 1.000 | 1.000 |
| Ethyl octanoate | 0.500 | 0.500 |
| Cis-3-hexenyl acetate | 1.500 | 1.500 |
| Cis-3-hexenol | 15.000 | 15.000 |
| Trans-3-cis-6-nonadienal | 0.150 | 0.150 |
| 2-Phenylethyl alcohol | 0.010 | 0.010 |
| γ-Decalactone | 0.200 | 0.200 |
| Ethyl maltol | 2.000 | 2.000 |
| Iso-butyric acid | 20500 | 20500 |
| Hexanoic acid | 0.800 | 0.800 |
| Propylene glycol (solvent) | 921.170 | 941.170 |
| Total | 1000.000 | 1000.000 |

As a result of evaluation, all 7 panelists reported that the flavor composition of Example 4 showed mango-like aroma higher in performance and natural feeling than the flavor composition of Comparative Example 3.

Example 5

Shampoo

A shampoo was prepared with the fruity and greenish fragrance composition obtained in Example 2 according to a prescription shown in Table 5 below. A compounding amount in the table is based on parts by weight. As the result, a shampoo with fruity and greenish aroma higher in natural feeling and good in performance was obtained.

TABLE 5

| Component | Amount |
|---|---|
| Triethanolamine polyoxyethylene laurylether sulfate | 16.0 |
| Lauryldimethylamine oxide | 5.0 |
| Betaine lauryldimethylamino acetate | 5.0 |
| Ethylene glycol distearate | 3.0 |
| Propylene glycol | 3.0 |
| Sodium benzoate | 0.5 |
| Fruity and greenish fragrance composition (Example 2) | 0.5 |
| Purified water | balance |
| Total | 100.0 |

Example 6

Body Shampoo

A body shampoo was prepared with the fruity and greenish fragrance composition obtained in Example 2 according to a prescription shown in Table 6 below. A compounding amount in the table is based on parts by weight. As the result, a body shampoo with fruity and greenish aroma higher in natural feeling and good in performance was obtained.

TABLE 6

| Component | Amount |
|---|---|
| Potassium laurate | 10.0 |
| Coconut oil fatty acid potassium salt | 10.0 |
| Sodium polyoxyethylene dilauryl ether sulfate | 7.0 |
| Ethylene glycol distearate | 3.0 |
| Laurylhydroxysulfobetaine | 2.0 |
| Propylene glycol | 7.0 |
| Hydroxypropylmethyl cellulose | 0.5 |
| Sodium benzoate | 0.5 |
| EDTA-disodium | 0.3 |
| Fruity and greenish fragrance composition (Example 2) | 1.0 |
| Purified water | balance |
| Total | 100.0 |

Example 7

Toothpaste

Toothpaste was prepared with the banana flavor composition obtained in Example 3 according to a prescription shown in Table 7 below. A compounding amount in the table is based on parts by weight. As the result, toothpaste with banana flavor higher in natural feeling and good in performance was obtained.

TABLE 7

| Component | Amount |
|---|---|
| Dicalcium phosphate | 20.0 |
| Sodium carboxylmethyl cellulose | 1.5 |
| Sodium saccharinate | 0.2 |
| Glycerin | 20.0 |
| Sodium lauryl sulfate | 1.0 |
| Hexylene glycol | 5.0 |
| Triclosan | 0.1 |
| Banana flavor composition (Example 3) | 1.0 |
| Purified water | balance |
| Total | 100.0 |

Example 8

Banana Flavored Beverage

A banana flavor beverage was prepared with the banana flavor composition obtained in Example 3 according to a prescription shown in Table 8 below. A compounding amount in the table is based on parts by weight. As the result, a banana flavored beverage higher in the natural feeling and good in performance was obtained.

TABLE 8

| Component | Amount |
|---|---|
| High-fructose corn syrup (75%) | 45.0 |
| Citric acid | 5.0 |
| 1-Ascorbic acid | 0.1 |
| Navel orange fruit juice | 5.0 |
| Banana flavor composition (Example 3) | 10.0 |
| Purified water | balance |
| Total | 100.0 |

Example 9

Mango Flavored Chewing Gum

A mango flavored chewing gum was prepared with the mango flavor composition obtained in Example 4 according to a prescription shown in Table 9 below. A compounding amount in the table is based on gram. As the result, a mango flavored chewing gum higher in the natural feeling and good in performance was obtained.

TABLE 9

| Component | Amount |
|---|---|
| Gum base | 100.0 |
| Sugar | 250.0 |
| Glucose | 40.0 |
| Corn syrup | 60.0 |
| Glycerin | 3.0 |
| Mango flavor composition (Example 4) | 2.0 |

What is claimed is:

1. A flavor composition or a fragrance composition containing at least one 2-methyl-2-pentenyl ester represented by a formula (I);

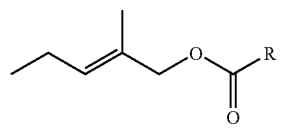

wherein, R represents a saturated hydrocarbon group having 2 to 9 carbon atoms, which may have an alkyl substituent, except for an isopropyl group.

2. The flavor composition or the fragrance composition according to claim 1, wherein the 2-methyl-2-pentenyl esters compound is added in an amount of 0.001 to 30% by weight in the flavor composition or fragrance composition.

3. Perfume or cosmetic products, toiletry products, bath agents, beverage or food products or medicines, wherein the flavor composition or the fragrance composition described in claim 1 or 2 is compounded in the range of 0.0001 to 3% by weight.

* * * * *